(12) United States Patent
Wong

(10) Patent No.: US 7,176,460 B1
(45) Date of Patent: *Feb. 13, 2007

(54) PASSIVE NDIR GAS SENSOR FIRE DETECTOR

(75) Inventor: Jacob Y. Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/367,439

(22) Filed: Mar. 3, 2006

Related U.S. Application Data

(63) Continuation-in-part of application No. 11/317,266, filed on Dec. 23, 2005, and a continuation-in-part of application No. 11/284,460, filed on Nov. 21, 2005.

(51) Int. Cl.
*G01N 21/35* (2006.01)

(52) U.S. Cl. .............................. 250/336.1; 250/339.15; 250/339.13; 250/339.01; 250/339.12; 340/328; 340/627; 340/629

(58) Field of Classification Search .......... 250/339.15, 250/339.3
See application file for complete search history.

(56) References Cited

U.S. PATENT DOCUMENTS

| | | | | |
|---|---|---|---|---|
| 5,486,810 A | * | 1/1996 | Schwarz | ...................... 340/521 |
| 5,721,430 A | * | 2/1998 | Wong | ..................... 250/339.13 |
| 5,800,360 A | * | 9/1998 | Kisner et al. | ................ 600/532 |
| 5,966,077 A | * | 10/1999 | Wong | .......................... 340/630 |
| 6,166,647 A | * | 12/2000 | Wong | .......................... 340/628 |
| 2005/0092067 A1 | * | 5/2005 | Petrovic et al. | ............ 73/31.05 |

* cited by examiner

*Primary Examiner*—David Porta
*Assistant Examiner*—Djura Malevic
(74) *Attorney, Agent, or Firm*—Wagner, Anderson & Brigt L.L.P; Roy L. Anderson

(57) ABSTRACT

A fire detector and method for detecting fires uses a passive NDIR sensor that generates a detector signal based upon either a 15μ absorption band of $CO_2$ or a 6.27μ absorption band of $H_2O$ and a signal processor which receives the detector signal and generates an alarm signal when a preselected criterion is met. The NDIR sensor relies upon a passive infrared source (such as a very thin film of black plastic material) with a high emissivity (e.g., approximately 1.0), a sample chamber with a low emissivity (e.g., approximately 0.03) thermally decoupled from the passive infrared source and an infrared detector located in a detector assembly thermally coupled to the sample chamber while a heat exchanger is thermally coupled to the sample chamber. Gas entering the sample chamber passes through the heat exchanger and both it and the infrared detector are at a lower temperature than that of the passive infrared source at an onset of a fire while the difference in temperatures between the passive infrared source and the detector increases during the onset of the fire. The sample chamber and the heat exchanger can be formed integrally from aluminum and their internal surfaces may be coated with a hydrophobic membrane.

20 Claims, 9 Drawing Sheets

A drawing showing schematically the design and implementation of a passive NDIR gas sensor without the use of an active radiation source and deployed as a low power fire detector.

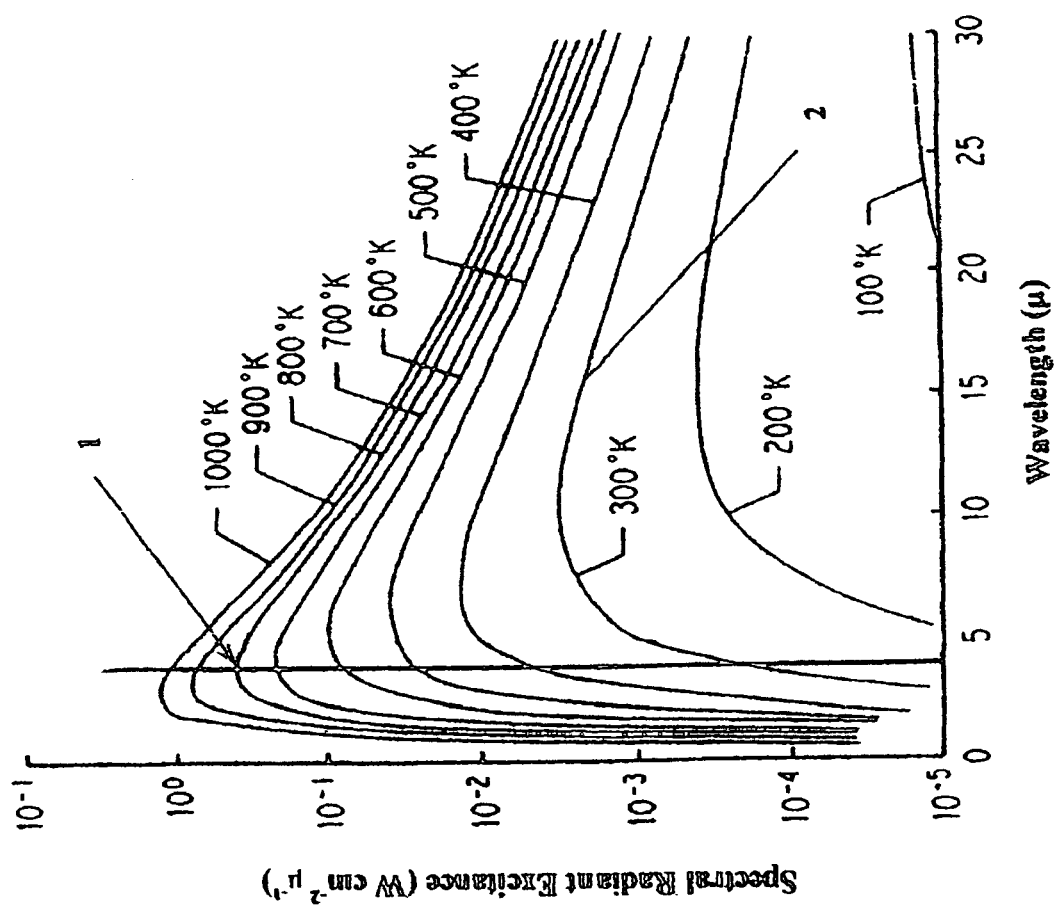
Figure 1. A graph showing the spectral radiant excitance of a blackbody source at temperatures 100 - 1,000 °K.

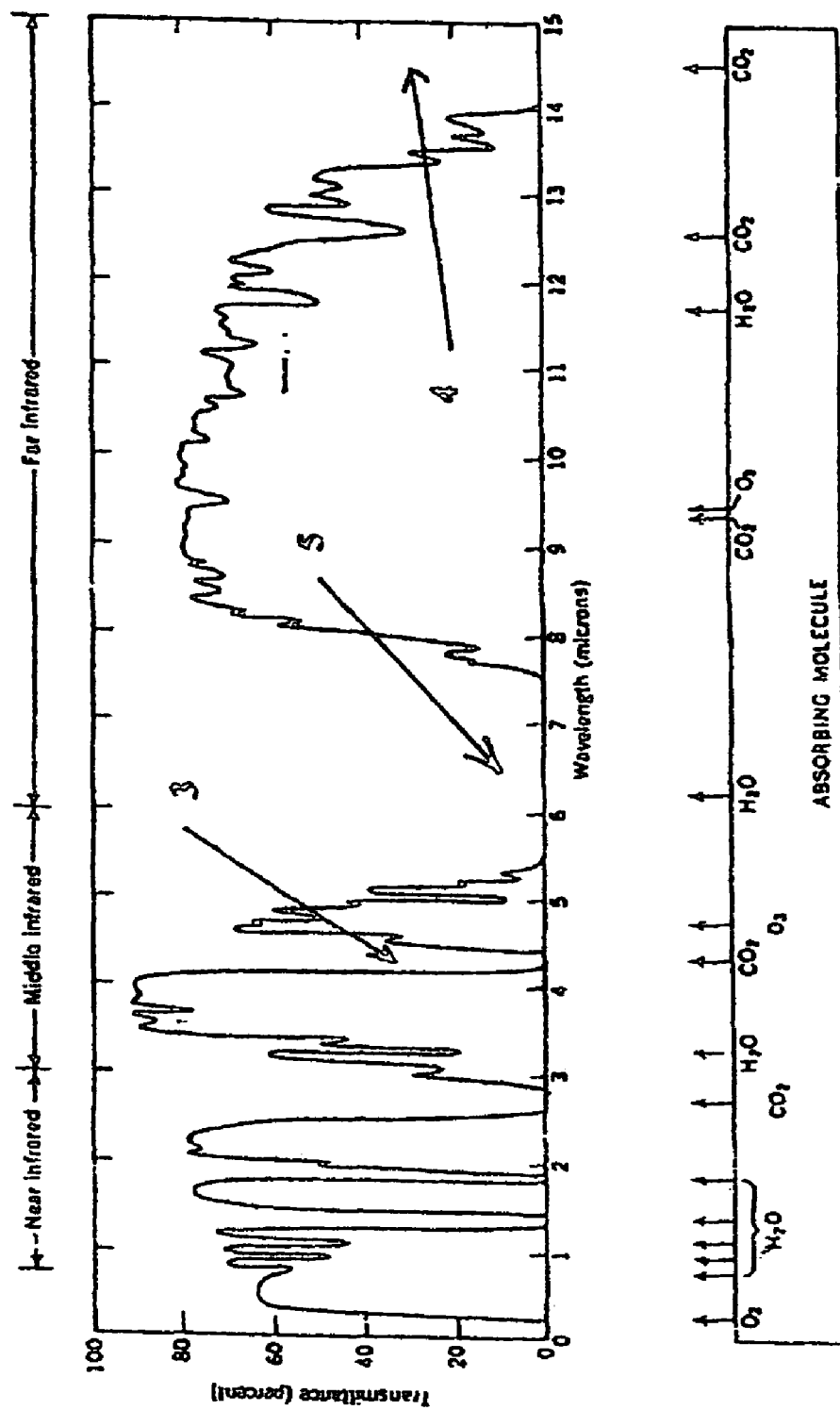
Figure 2. A graph showing the transmittance of the atmosphere for a 6,000 ft horizontal path at sea level showing the presence of prominent CO2 absorption bands at 4.26 μ and ~15 μ and a very strong water vapor absorption band at 6.27 μ.

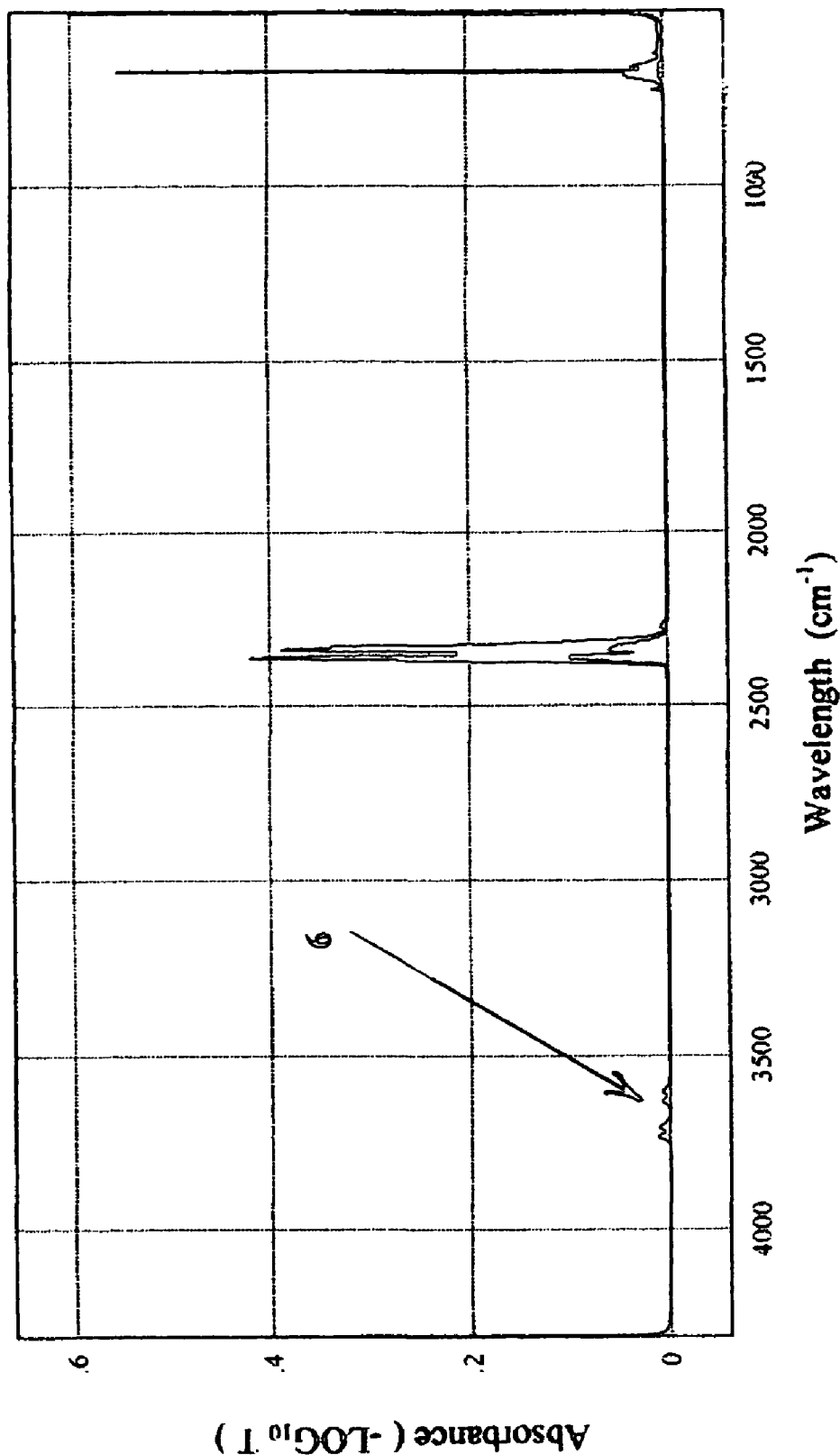
Figure 3. A graph showing the absorbance of $CO_2$ gas at wavelengths from ~2 μ - 20 μ (5,000 $cm^{-1}$ - 500 $cm^{-1}$). Only the 4.26 μ and ~15 μ absorption bands of $CO_2$ are shown to be prominently present in this spectral region.

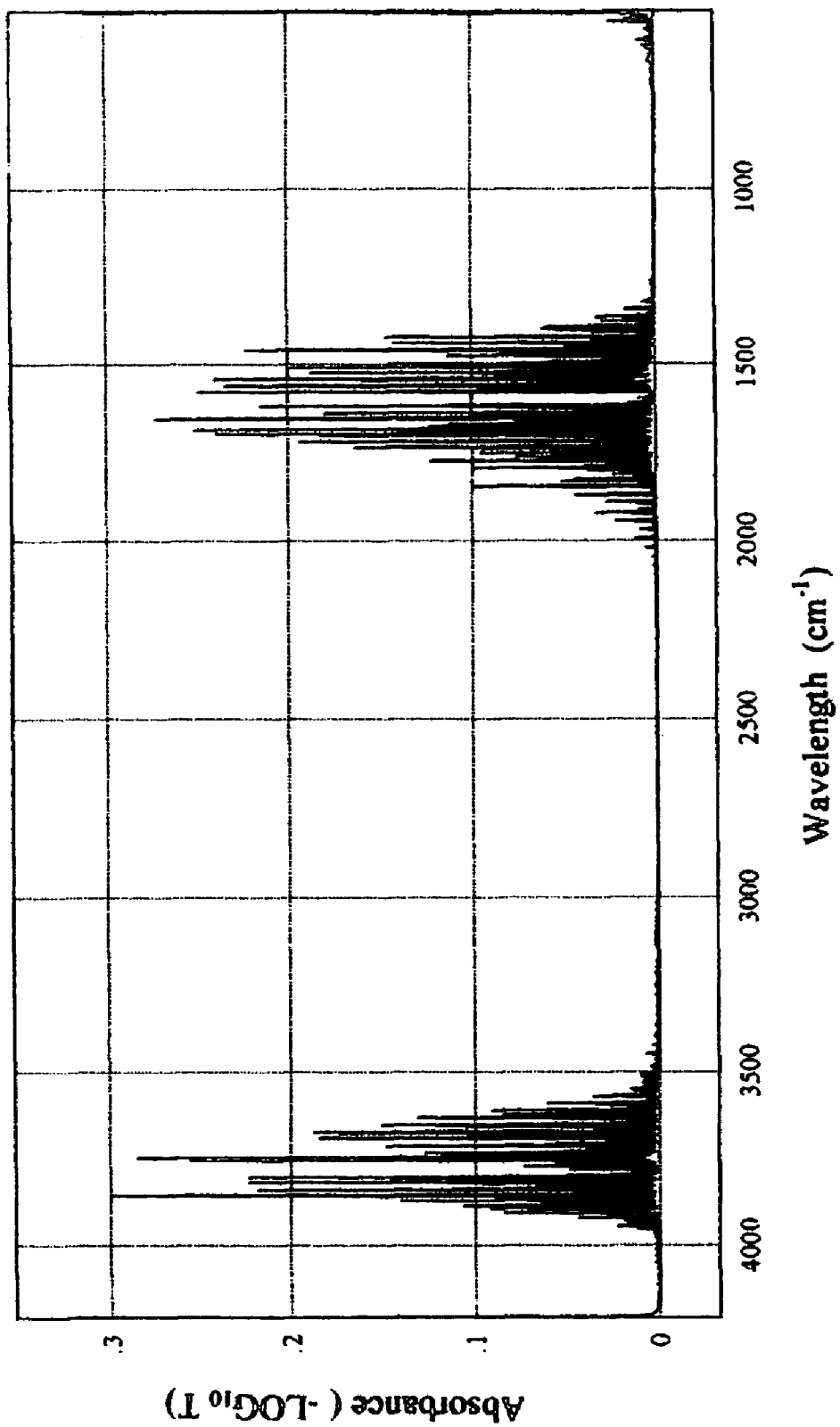
Figure 4. A graph showing the absorbance of water vapor (H2O) at wavelengths from ·2 μ - 20 μ (5,000 cm-1 - 500 cm-1) showing the strong absorption bands at 2.67 μ and 6.27 μ.

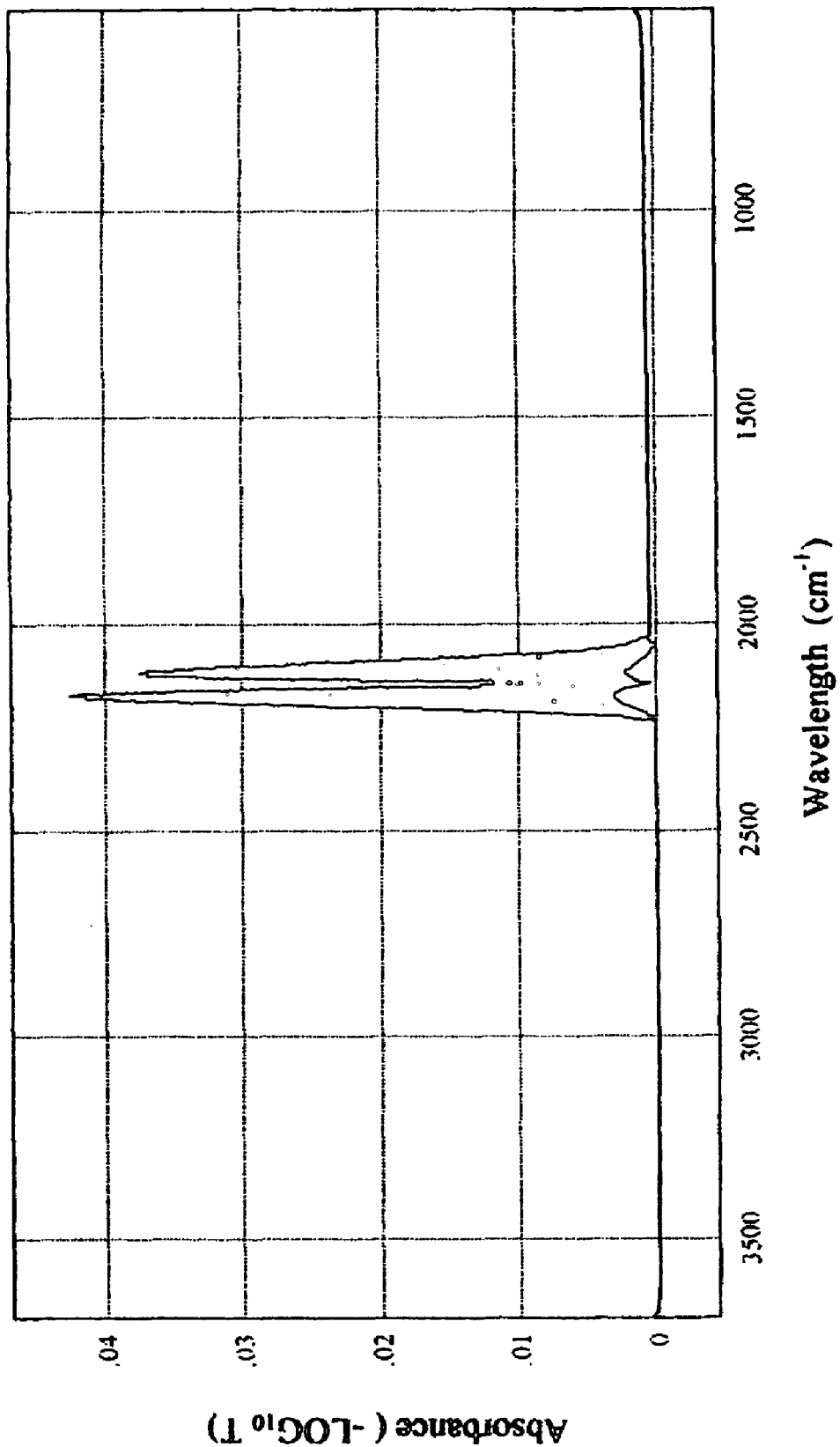
Figure 5. A graph showing the absorbance of Carbon Monoxide (CO) gas at wavelengths from ~2 μ – 20 μ (5,000 cm-1 – 500 cm-1) showing an absorption band at 4.65 μ.

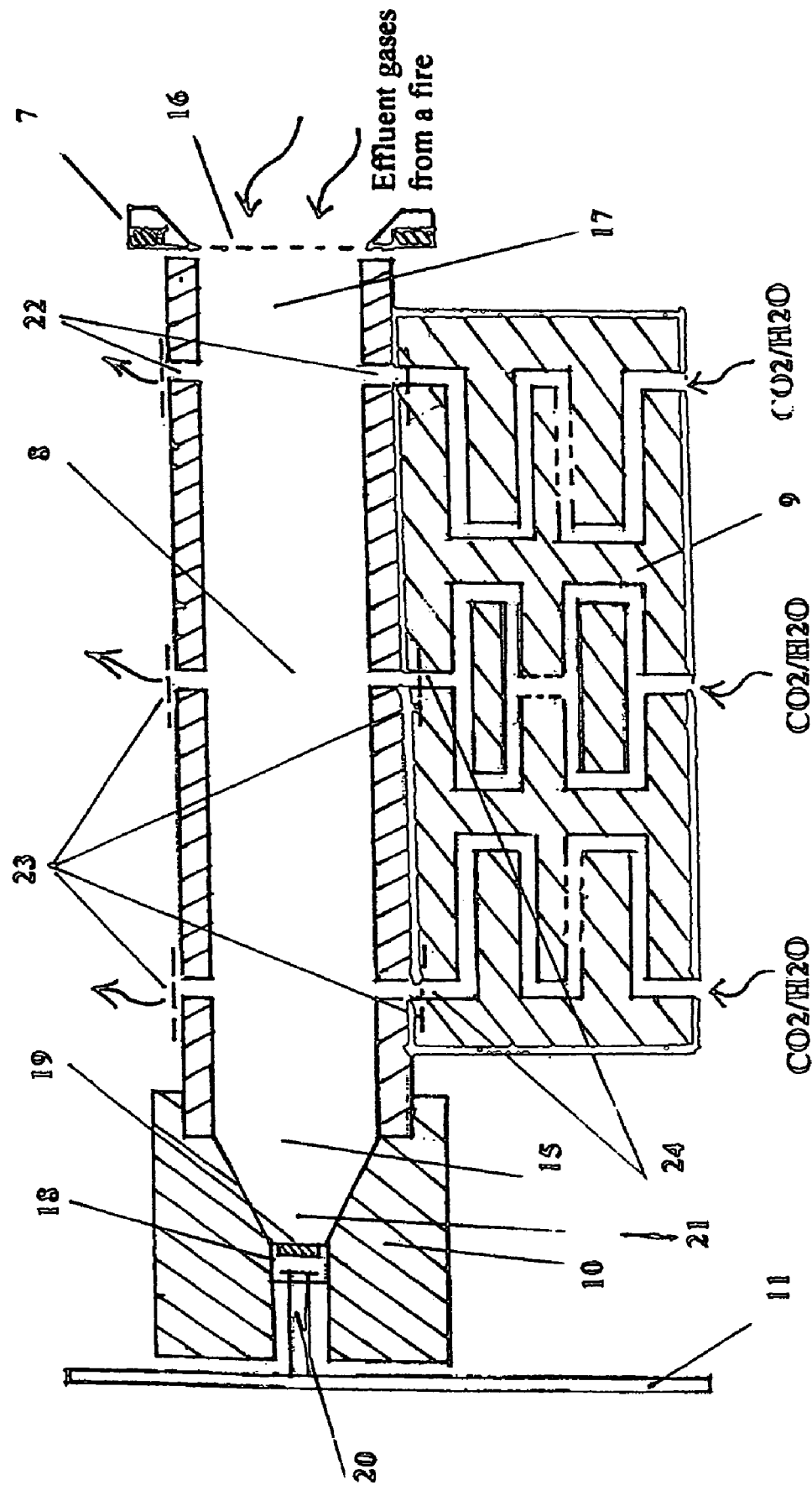
Figure 6. A drawing showing schematically the design and implementation of a passive NDIR gas sensor without the use of an active radiation source and deployed as a low power fire detector.

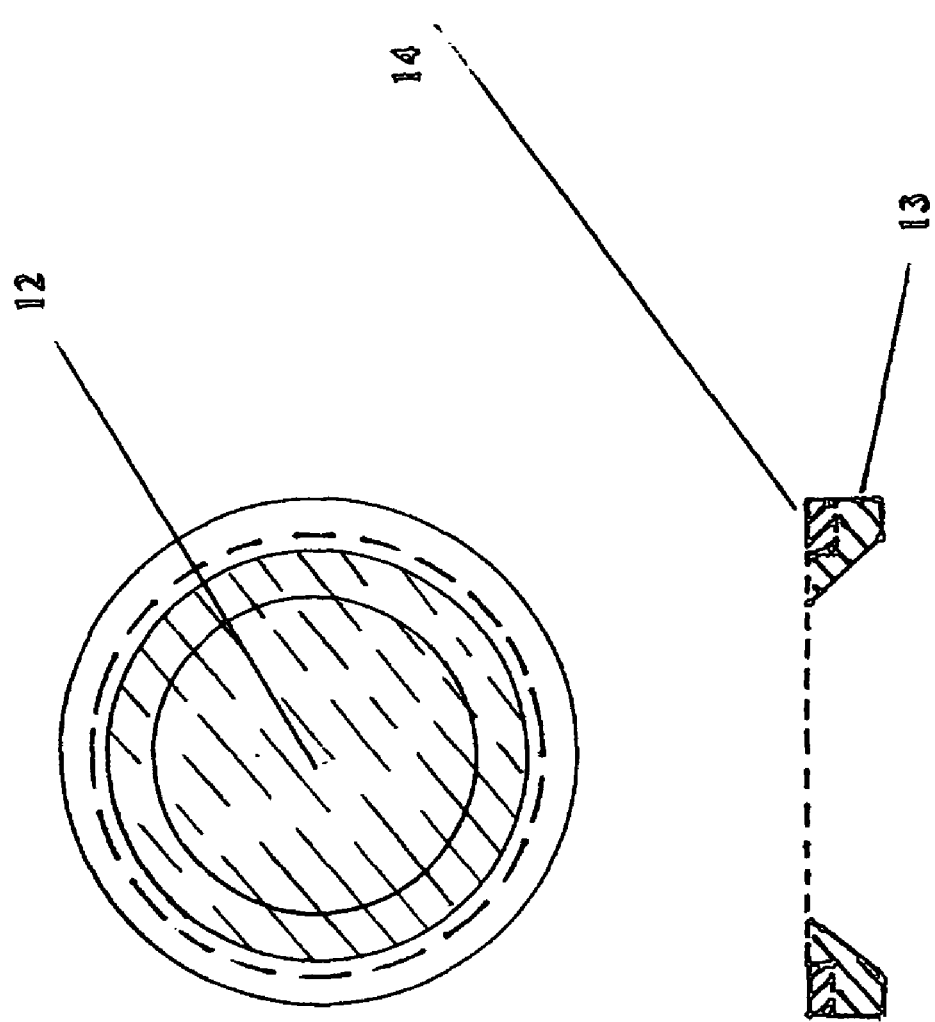
Figure 7. A drawing showing the details for the construction of a passive infrared source using a very thin (~0.001") black plastic film stretched and retained onto a plastic annular base with a tightly fitted plastic ring.

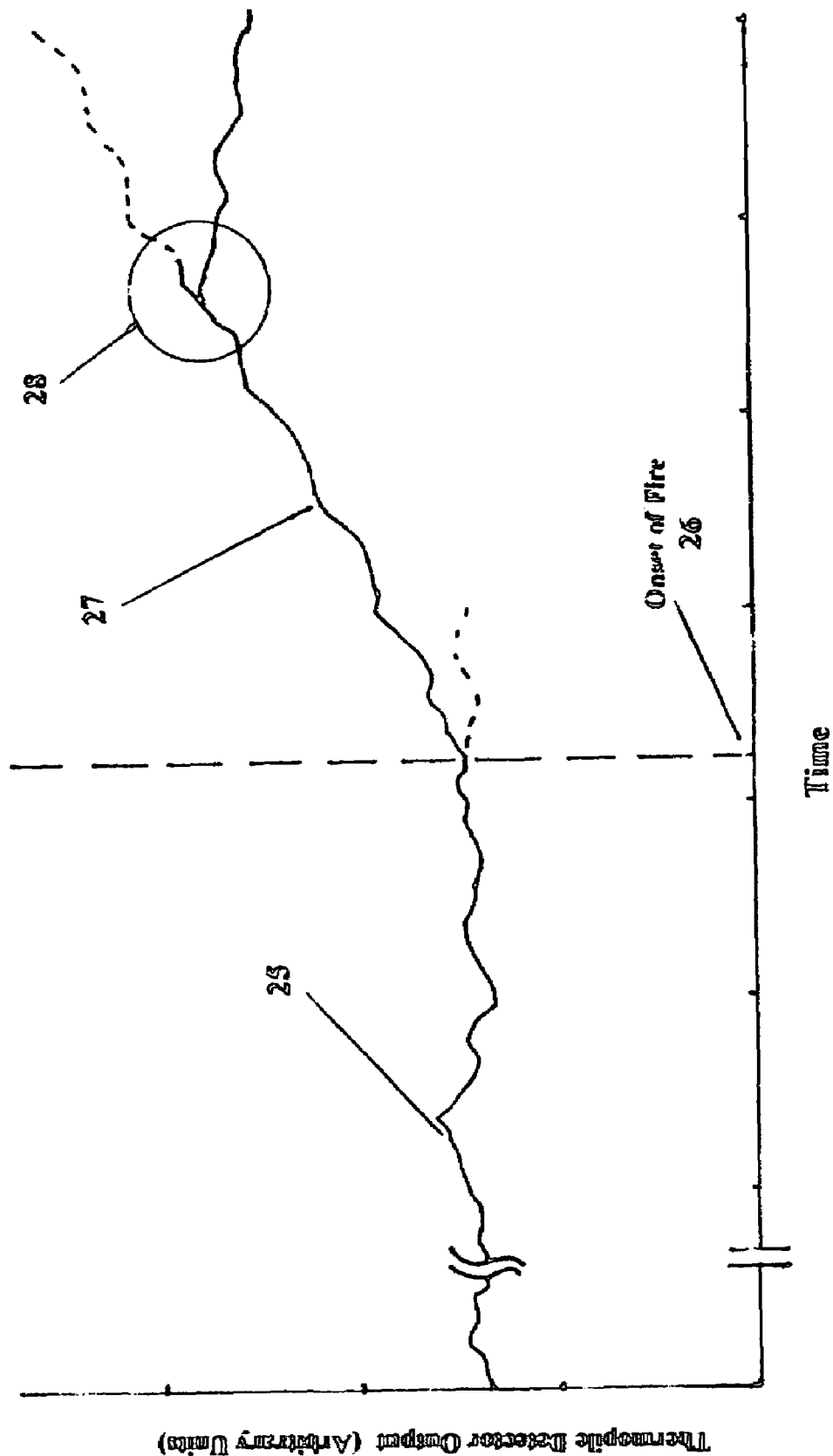
Figure 8. A graph showing the anticipated fire signature for the onset of a fire as reflected in the thermopile detector output versus time for the passive NDIR gas sensor fire detector.

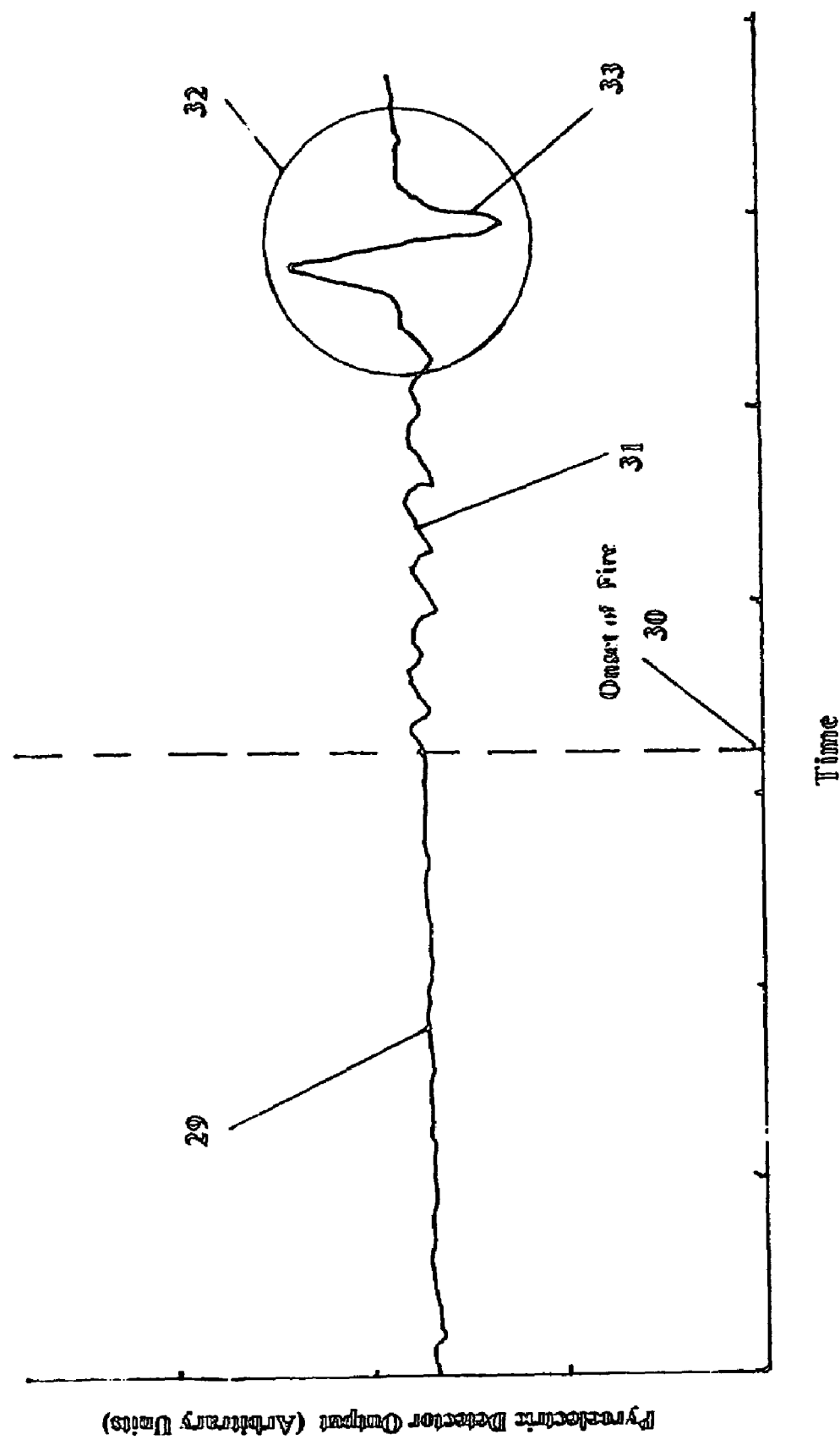
Figure 9. A graph showing the anticipated fire signature for the onset of a fire as reflected in the pyroelectric detector output versus time for the passive NDIR gas sensor fire detector.

PASSIVE NDIR GAS SENSOR FIRE DETECTOR

CROSS-REFERENCE TO RELATED APPLICATION

This application is a continuation-in-part application of U.S. patent application Ser. Nos. 11/317,266 filed Dec. 23, 2005 entitled "Passive NDIR Carbon Dioxide Sensor Fire Detector" and Ser. No. 11/284,460 filed Nov. 21, 2005 entitled "Ultra Low Power NDIR Carbon Dioxide Sensor Fire Detector," the disclosures of which are specifically incorporated herein by reference.

FIELD OF THE INVENTION

The present invention is in the field of gas analysis and more particularly relates to a passive (no active radiation source used) NDIR gas sensor designed to be used as a compact, low power, low cost, fast responding and false alarm resistant fire detector.

BACKGROUND OF THE INVENTION

The Non-Dispersive Infrared ("NDIR") technique has long been considered as one of the best methods for gas measurement. In addition to being highly specific, NDIR gas analyzers are also very sensitive, stable, reliable and easy to maintain. The major drawback of the NDIR gas measurement technique has been its relatively expensive implementation and high power consumption.

Ever since the NDIR technique of gas measurement was first introduced and practiced in the mid 1950's, a large number of improved measurement techniques based upon the NDIR principle for gas detection have been proposed and successfully demonstrated. The most notable advances over the years in this field are summarized as follows.

Burch et al. (U.S. Pat. No. 3,793,525) and Blau et al. (U.S. Pat. No. 3,811,776) in 1974 were the first to advance a so-called "Double Beam" technique for NDIR gas measurement by taking advantage of the principle of nonlinear absorption for some strongly absorbing gases such as $CO_2$ to create a reference channel. Shortly thereafter, this "Double Beam" NDIR gas sensor technique was greatly simplified with the use of two interposed spectral filters (one absorbing and one neutral) to create a sample and a reference detector channel. Subsequent NDIR gas sensors, designed using this technique, have enjoyed good output stability as a function of time.

In U.S. Pat. No. 4,578,762 (1986) Wong advanced the first self-calibrating NDIR $CO_2$ analyzer using a novel two-wheel chopper and mirror arrangement. Another improved type of such gas analyzer is shown and described in U.S. Pat. No. 4,694,173 (1987) by Wong. This gas analyzer has no moving parts for effecting the interposition of spectral filters or absorbing and non-absorbing cells to create both a sample and reference detector channel as in the NDIR gas analyzers described earlier.

In U.S. Pat. No. 5,163,332 (1992), Wong advanced the so-called "wave-guide" sample chamber for simplifying NDIR gas sensors into ones that are compact, rugged and low-cost while still maintaining their superior performance characteristics.

All of the NDIR gas analyzers described above for the measurement of the concentrations of one or more gases in a mixture perform well functionally and have contributed overwhelmingly to the overall technical advancement in the field of gas analysis during the past two decades. They have been widely accepted in both the medical and industrial communities. Despite their undisputed success over the years, there still remains an important application, namely the commonplace household fire detector, not successfully realized to date due to the fact that NDIR gas sensors are still too costly and consume too much power when used as sentinel fire detectors.

A majority of fire detectors in use today in almost all public buildings and private dwellings are in essence smoke detectors as they only detect the smoke resulting from a fire. The most common smoke detectors currently in use belong to two types. The first type is the so-called ionization smoke detector best for detecting invisible smoke particles ranging in size from <1.0 microns to ~5 microns. The second type is called the photoelectric smoke detector best for detecting visible smoke particles >5 microns in size. For the past two decades, the ionization smoke detectors because of their low cost (<$10 retail) have dominated the fire market and are in use in over 90% of households. In recent years, photoelectric smoke detectors, because of their higher cost (<$30 retail), have fallen significantly behind in sales. Combined ionization and photoelectric smoke detectors, albeit at an even higher cost (~$40 retail), have also been available for quite sometime but have not to date received much acceptance by the public.

Despite their low cost, relatively maintenance-free operation and wide acceptance by the buying public, the smoke detectors in widespread use today are not without problems and certainly are far from being ideal. One of the biggest problems with ionization smoke detectors besides being radioactive (Americium-241) is their frequent false-alarm. By the nature of its operational principle, any micron-size particulate matter other than smoke from an actual fire can set off the alarm. Kitchen grease particles generated by a hot stove is one classic example. Over-zealous dusting of objects and/or furniture near the detector is another. Frequent false-alarms are not just a harmless nuisance; some people actually disable their smoke detectors by temporarily removing the battery in order to escape such annoying episodes. This latter situation could be outright dangerous especially when these people forget to rearm their smoke detectors.

Another significant drawback for the current ionization smoke detector is its relatively slow speed to alert people of a fire. There are several factors that contribute to this particular drawback. The first fact is the detector trigger threshold for smoke which directly affects its response time to the onset of a fire. No doubt a lower trigger threshold would mean a faster fire detector. However, it also means more frequent annoying false alarms for the user. The second factor is the particular placement of the detector with respect to the spot where fire breaks out. Unlike ordinary gases, smoke is actually a complex sooty molecular cluster that consists mostly of carbon. It is much heavier than air and thus diffuses much slower than the gases we encounter everyday. Therefore, if the detector happens to be at some distance from the location of the fire, it will be awhile before enough smoke gets into the sampling chamber of the smoke detector to trigger the alarm. A third factor is the nature or type of the fire itself. Although smoke usually accompanies fire, the amount produced can vary significantly depending upon the composition of the material that catches fire. For example, oxygenated fuels such as ethyl alcohol and acetone give less smoke than the hydrocarbon from which they are derived. Thus, under free-burning conditions oxygenated fuels such as wood and polymethylmethacrylate give substantially less smoke than hydrocarbon polymers such as polyethylene and polystyrene. As a matter of fact, a small number of pure fuels, namely carbon monoxide, formaldehyde, metaldehyde, formic acid and methyl alcohol, burn with non-luminous flames and do not produce smoke at all.

Since fire is an oxidation process, detection of a sudden increase in ambient levels of one or more of the three principal effluent gases of fire, namely $CO_2$, $H_2O$ and Carbon Monoxide (CO) is an effective way of detecting same. For the past 20 years, the use of $CO_2$ sensor as a standalone fire detector or in combination with smoke detectors has been continually advocated by experts as the most effective fire detector. The reason is two-fold. First, there is a significant advantage of using a $CO_2$ sensor rather than a smoke detector for fire initiation detection. The mobility of $CO_2$ as a gas is far greater than that for smoke which is much heavier. Therefore $CO_2$ diffuses from the fire to the detector in a much shorter time leading to a faster response time for enunciating fire. Second, over the past two decades, compact, low cost and reliable NDIR type $CO_2$ sensors have become readily available. As a matter of fact, over the same period of time, a large number of deployment schemes, fire fighting techniques and fire control strategies, which use either a standalone NDIR $CO_2$ sensor or in combination with smoke detectors, have been advanced. The most notable proposals of such are summarized as follows.

In U.S. Pat. No. 5,053,754 (1991), Wong advanced the first NDIR $CO_2$ sensor used as a standalone fire detector. A fire detection system using at least two NDIR $CO_2$ sensors positioned at spaced locations in an area for pin-pointing the exact origin of a fire was described in U.S. Pat. No. 5,079,422 (1992) by Wong. Meanwhile a standalone and compact low-cost fire detector which responds quickly to an increase in the concentration of $CO_2$ gas in the ambient air was advanced in U.S. Pat. No. 5,103,096 (1992) by Wong. In U.S. Pat. No. 5,369,397 (1994), an adaptive fire detector taking advantage of the capability of an NDIR $CO_2$ sensor for computing the rate of $CO_2$ increase to shorten the response time for enunciating the onset of a fire was also advanced by Wong. In U.S. Pat. No. 5,592,147 (1997), an NDIR $CO_2$ sensor used cooperatively in combination with a photoelectric smoke detector for significantly reducing false alarms was put forth by Wong. Also in 1997 and in U.S. Pat. No. 5,691,704, Wong disclosed another NDIR $CO_2$ photoelectric smoke detector combination fire detector with special software which can be designed into a single semiconductor chip for cost reduction and further false alarm improvement. In U.S. Pat. No. 5,767,776 (1998), Wong disclosed the design of an NDIR $CO_2$ and smoke detector combination which reduces the maximum average response time to less than 1.5 minutes. Further refinement of this design was described in U.S. Pat. No. 5,798,700 (1998) by Wong, U.S. Pat. No. 5,945,924 (1999) by Marman et al. and U.S. Pat. No. 5,966,077 (1999) by Wong. Finally, a method for dynamically adjusting criteria for detecting fire through smoke concentration using an NDIR $CO_2$ and smoke detector combination was described by Wong in U.S. Pat. No. 6,107,925 (2000).

Despite the continual and persistent advocacy of many fire experts that an NDIR $CO_2$ sensor, either as a standalone fire detector or in combination with a smoke detector, is better than present-day smoke detectors in both speed of response and proof against false alarms, it has yet to be exploited as a superior fire detector. The reasons are twofold. First, even with the drastic cost reduction for present-day NDIR $CO_2$ sensors, the cost is still far too high when compared with ionization type smoke detectors. Second and by far the most significant is the fact that being an NDIR gas sensor, its active infrared source uses far too much power when operated continuously. Because of this, it is not suitable for use in almost any circumstance, whether it is residential, commercial or industrial.

SUMMARY OF THE INVENTION

The present invention is generally directed to a fire detector that uses a passive sensor that generates a detector signal based upon either a 15μ absorption band of $CO_2$ or a 6.27μ absorption band of $H_2O$ and a signal processor which receives the detector signal and generates an alarm signal when a preselected criterion is met.

In a first, separate group of aspects of the present invention, the signal processor relies upon a detection algorithm based upon a trending pattern of the detector signal indicative of the onset of a fire, such as a sudden steady increase in the amplitude of the detector signal (converted to a DC signal) caused by rising hot air of a potential fire as the fire first breaks out and may include a substantial drop in the detector signal strength when an effluent byproduct gas from the fire and smoke particles subsequently arrive near the sensor as the fire persists.

In a second, separate group of aspects of the present invention, a fire detector (that may be used as a standalone smoke detector or combined with a smoke detector) is provided with a passive NDIR sensor having a passive infrared source (such as a very thin film of black plastic material) with a high emissivity (e.g., approximately 1.0), a sample chamber with a low emissivity (e.g., approximately 0.03) thermally decoupled from the passive infrared source and an infrared detector located in a detector assembly thermally coupled to the sample chamber while a heat exchanger is thermally coupled to the sample chamber and a signal processor receives the detector signal and generates an alarm signal when a preselected criterion is met. Gas entering the sample chamber passes through the heat exchanger and both it and the infrared detector are at a lower temperature than that of the passive infrared source at an onset of a fire while the difference in temperatures between the passive infrared source and the detector increases during the onset of the fire. The sample chamber and the heat exchanger can be formed integrally from aluminum and their internal surfaces may be coated with a hydrophobic membrane.

In a third, separate group of aspects of the present invention, a fire detector uses a passive $H_2O$ sensor to generate a detector signal representative of attenuation of radiation observed normally from a passive source to the passive $H_2O$ sensor having a passive $H_2O$ detector, a filter for a 6.27μ absorption band of $H_2O$ and electronics for receiving the detector signal and generating an alarm signal when a preselected criterion is detected by an algorithm based at least in part upon the detector signal, there being an optical aperture to define a subtended solid angle by the passive source.

In a fourth, separate group of aspects of the present invention, a method for generating an alarm signal in response to a fire uses a passive gas sensor to generate a detector signal based upon either a 15μ absorption band of $CO_2$ or a 6.27μ absorption band of $H_2O$ and generates an alarm signal when a preselected criterion indicative of the onset of a fire is met based upon an analysis of the detector signal. The gas sensor may be a very thin film of black plastic material with a high emissivity that is heated during the onset of the fire by a hot gas effluent from the fire while other hot gas effluent from the fire is cooled by a heat exchanger and then passed into a sample chamber thermally decoupled from the passive infrared source so that gas entering the sample chamber as well as the infrared detector are at a lower temperature than the temperature of the passive infrared source at an onset of a fire.

Accordingly, it is an object of the present invention to advance a new design for an NDIR gas sensor aimed at further lowering its cost and, more importantly, reducing its power consumption so that it can in fact be used as a fire detector. It is also an object of the present invention to cater the design of this NDIR gas sensor to be suitable for use as a low power, low cost, false alarm resistant and fast response fire detector.

These and further objects and advantages will be apparent to those skilled in the art in connection with the drawings and the detailed description of the preferred embodiment set forth below.

BRIEF DESCRIPTION OF THE DRAWINGS

FIG. 1 is a graph showing the spectral radiant excitance of a blackbody source at temperatures 100–1,000° K.

FIG. 2 shows the transmittance of the atmosphere for a 6,000 ft horizontal path at sea level showing the presence of prominent $CO_2$ absorption bands at 4.26μ and ~15μ and a very strong water vapor absorption band at 6.27μ.

FIG. 3 shows the absorbance of $CO_2$ gas at wavelengths from ~2μ–20μ (5,000 cm−1–500 cm−1). Only the 4.26μ and ~15μ absorption bands of $CO_2$ are shown to be prominently present in this spectral region.

FIG. 4 shows the absorbance of water vapor at wavelengths from ~2μ–20μ (5,000 cm−1–500 cm−1) showing the strong absorption bands at 2.67μ and 6.27μ.

FIG. 5 shows the absorbance of Carbon Monoxide (CO) gas at wavelengths from ~2μ–20μ (5,000 cm−1–500 cm−1) showing an absorption band at 4.65μ.

FIG. 6 shows schematically the design and implementation of a passive NDIR gas sensor without the use of an active radiation source and deployed as a low power fire detector.

FIG. 7 shows the details for the construction of a passive infrared source using a very thin (~0.001") black plastic film stretched and retained onto a plastic annular base with a tightly fitted plastic ring.

FIG. 8 shows the anticipated fire signature for the onset of a fire as reflected in the thermopile detector output versus time for the passive NDIR gas sensor fire detector.

FIG. 9 shows the anticipated fire signature for the onset of a fire as reflected in the pyroelectric detector output versus time for the passive NDIR gas sensor fire detector.

DETAILED DESCRIPTION OF THE INVENTION

Over the past three decades, the design of NDIR $CO_2$ gas sensors has invariably used the strong $CO_2$ absorption band at 4.26μ infrared. This band is not only strong, it is also very specific. In other words, no other gases, other than some extremely weak water vapor absorption continuum, have absorption bands within it. Thus, interferences caused by the presence of other gases to the $CO_2$ measurement are virtually nonexistent. In accordance with the conventional wisdom of NDIR sensor design, the most optimum infrared source to use for $CO_2$ detection should have a blackbody temperature at around 800–900° K, which has its peak spectral radiant excitance located at around 4.26μ according to Planck's Radiation Law (see FIG. 1). Because of the aforementioned facts, NDIR $CO_2$ sensors are not difficult to design and they were among the earliest NDIR gas sensors manufactured and available for sale to the public circa around mid 1950's. However, the use of a high temperature infrared source for the design of a NDIR $CO_2$ sensor using the 4.26μ absorption band is the main reason why the power consumption for such a sensor is invariably high and cannot easily be lowered. Since most fire detectors have always been battery-operated, requiring very low power consumption for their continuous operation, this is also the principal reason why NDIR $CO_2$ sensors to date have not found their way to be used as fire detectors.

Although water vapor and CO are also principal effluent gases from a fire, detection of their sudden increased presence is seldom used as a means to signal the onset of a fire. There are several reasons to explain that. Let us start off with CO. CO is invariably generated in a lesser quantity than $CO_2$ at the beginning of a combustion process unless the latter is very sluggish (slow burning or incomplete combustion), like in a smoldering fire. However, once the combustion or fire takes hold with oxidation being the primary process, there is far more $CO_2$ being produced than CO. It is only when the fire temperature reaches ~600° C. or above that more CO is produced at the expense of the forming of $CO_2$ and Carbon. Since normally the CO concentration is very low at home or at work (~a few ppm), the sudden increase of CO concentration above a certain threshold, say 20 ppm, as detected by an NDIR gas sensor, could be used to indicate the onset of a fire, though more likely to be only that for a smoldering or slow-burning one. Whereas NDIR $CO_2$ sensors with adequate sensitivity to detect $CO_2$ concentration level increase in a fire (+/−50 ppm's) are easy to build, it is not so for NDIR CO sensors, especially those with sensitivity of just a few ppm's. The reasons are explained as follows.

First, the CO absorption band at 4.65μ is approximately ten times weaker than the 4.26μ $CO_2$ counterpart (see FIGS. 3 and 5). Second, there are significant amounts of interferences due to adjacent $CO_2$ and $H_2O$ absorption bands that affect the CO modulation at 4.65μ which make it difficult to detect small amounts of CO, like in a few ppm's or less. Third, small, reliable and inexpensive miniature light bulbs, which can be used as very effective infrared sources to build NDIR $CO_2$ sensors, cannot be used for CO due to the very low transmission of the light bulb glass envelop at 4.65μ. Putting all of these together, a very low-cost and high sensitivity NDIR CO gas sensor has to date not been available for purchase in the marketplace for use as a possible fire detector. Needless to say, only optical gas sensors like the NDIR type are stable enough for use as fire detectors. Relatively low cost and small electrochemical CO sensors are readily available for purchase in the marketplace. However, unlike NDIR gas sensors, they are known to be unstable over relatively short periods of time and are therefore not suitable for use as fire detectors.

Since almost all combustible materials contain the hydrogen atom (H) bonded covalently with carbon and Oxygen, the generation of $CO_2$ molecules during the oxidation process of a fire invariably involves also the generation of $H_2O$ molecules. This is very much likened to the metabolism of food stuff, which contains both oxygen and hydrogen atoms along with other lesser quantity molecules, inside our body. The end products of a normal or healthy metabolism are $CO_2$ and $H_2O$ plus the output of energy. The reasons why a sudden increase in $H_2O$ concentration level has not been singled out to date for detecting the onset of a fire are also many fold. First and foremost, whereas indoor CO concentration is relatively stable and low, the presence of $H_2O$ in the air (indoors or out) is weather-related and varies significantly over short periods of time. Furthermore, the concentration level can be very high, varying from a few thousand ppm's when the air is very dry to over 50,000 ppm's when it is very wet or humid. Second, a low cost and long-term stable humidity sensor is at present simply not available for use as a reliable fire detector. Third, even in the presence of a fire when $H_2O$ molecules are being abundantly produced, the concentration level of $H_2O$ might not even be measured accurately at any time by a humidity sensor due to the fact that $H_2O$ condenses readily on any cold surfaces and thereby disappears without a trace. Thus, due to the peculiar behavior of $H_2O$ molecules and the lack of adequate, especially with respect to long-term stability, humidity sensors available today, a sudden increase in $H_2O$ concentration level has not been used as a means to signal the onset of a fire.

To overcome this seemingly untenable situation, the present invention proposes finding another specific absorption band for $CO_2$ such that the operating temperature of an infrared source used for its detection can be much lower than that when the conventional $4.26\mu$ absorption band of $CO_2$ is used. Therefore, instead of using the strong $4.26\mu$ absorption band of $CO_2$ to design the sensor of the present invention, the present invention uses the strong and much broader absorption band of $CO_2$ at $14.9$–$16.2\mu$ which shall be referred to as the "absorption band at $\sim15.0\mu$" or "$15\mu$ absorption band of $CO_2$." This $15\mu$ absorption band of $CO_2$ is also very specific. Furthermore, it actually is slightly stronger than the $4.26\mu$ one.

FIG. 1, shows the graph depicting the spectral radiant excitance of a blackbody source at temperatures $100$–$1,000°$ K. The peak spectral radiant excitance for a $800°$ K blackbody is at $4.26\mu$ which is also the center wavelength (CWL) for the $4.26\mu$ absorption band of $CO_2$ as indicated by the vertical line 1. This confirms the fact that the optimum temperature of the an infrared source using the $4.26\mu$ absorption band for designing an NDIR $CO_2$ gas sensor is $\sim800°$ K. Also shown in FIG. 1 is the Planck's radiation curve for a $300°$ K blackbody 2, which has a peak spectral radiant excitance at $\sim10$–$15\mu$ centering approximately on the $15\mu$ absorption band of $CO_2$. This is the reason why a much lower temperature infrared source can actually be used for the design of an NDIR $CO_2$ gas sensor when one uses the $15\mu$ absorption band of $CO_2$.

FIG. 2 shows the transmittance of the atmosphere for a $6,000$ ft. horizontal path at sea level showing the presence of the $CO_2$ absorption bands at both $4.26\mu$, 3, and $\sim15\mu$, 4. Also shown in FIG. 2 is the strong absorption band of $H_2O$ at $6.27\mu$, 5. The $4.65\mu$ absorption band of CO, however, cannot be seen in FIG. 2 due to the very low concentration of the gas in the atmosphere. A more quantitative portrayal for these two $CO_2$ bands, the strong $6.27\mu$ band of water vapor and the $4.65\mu$ of CO are depicted in FIG. 3, FIG. 4 and FIG. 5 respectively. In FIG. 3, the absorbance of $CO_2$ is plotted against wavelength for a gas sample having an absorber concentration of $0.01$ atm-cm in Nitrogen and at 1 atmosphere total pressure. One can see from FIG. 3 that these two $CO_2$ bands have roughly the same strength. One can also see from FIG. 3 that with the exception of a couple of weaker bands at $\sim2.70\mu$, 6, there are no other $CO_2$ absorption bands present in the spectral region of $2\mu$–$20\mu$.

In FIG. 4, the absorbance of the strong $6.27\mu$ ($1,595$ cm$-1$) absorption band of $H_2O$ is plotted against wavelength for a gas sample having an absorber concentration of $0.1$ atm-cm in Nitrogen and at 1 atmosphere total pressure. Comparing this water vapor absorption band with those of $CO_2$ (see FIG. 3), one can see that the former is somewhat weaker than either of the latter.

In FIG. 5, the absorbance of the relatively weak $4.65\mu$ absorption band of CO is plotted against wavelength for a gas sample having an absorber concentration of $0.01$ atm-cm in Nitrogen and at 1 atmosphere total pressure. One can see that the strength of this absorption band for CO is approximately 10 times weaker than the $4.26\mu$ band of $CO_2$ (see FIG. 3).

While the use of the $15\mu$ $CO_2$ band for the design an NDIR $CO_2$ sensor enables one to use much lower temperature infrared sources with values hovering around $300°$ K, it is even possible to give up the use of an active radiation source altogether and use instead a passive one. By an active radiation source is meant, according to the teaching of U.S. Pat. No. 5,053,754 (1991) by Wong, a miniature conductor that is heated by an electrical current and that emits a spectrum of radiation approximating that of a blackbody source. Thus an active infrared source can assume a number of forms, shapes, sizes and conductive materials. Common active infrared sources include miniature light bulbs, semiconductor resistors, metallic resistors such as nichrome wires, infrared light emitting diodes etc. Opposite to an active infrared source is a passive infrared source. Although a passive infrared source does not require any electrical current to activate and it operates at much lower temperatures, it also emits a spectrum of radiation approximating that of a blackbody. Thus a portion of a wall or ceiling at room temperature $T_0$ is a passive infrared source having a blackbody temperature of $T_0$. A block of wood painted black (emissivity, $\epsilon$, $\sim1.0$) sitting in a room at temperature $T_0$ is also a passive infrared source with a blackbody temperature very close to $T_0$. Without the need to pass electrical current through it in order to activate same, a passive blackbody, as long as it is above absolute zero ($0°$ K) in temperature, spontaneously emits radiation on its own according to the Planck's Radiation law. However, the high range in blackbody temperature for a practical passive source is limited to no more than $300$–$350°$ K or $23$–$77°$ C. as objects in an environ such as an indoor enclosure seldom exceed $350°$ K or $77°$ C.

Several things need to be heeded before one can successfully use a passive infrared source to design an NDIR gas sensor fire detector. First, as alluded to earlier, one has to choose the right absorption band for any effluent gas to use with this source. Thus for $CO_2$, it would be very difficult if not impossible to use the $4.26\mu$ band for designing the NDIR $CO_2$ sensor with a $300°$ K passive source as the latter has hardly any energy emitted at $4.26\mu$. On the other hand, the $15\mu$ $CO_2$ band is just about perfect as the peak spectral excitance is located at around the same spectral region for $300°$ K passive infrared sources. Needless to say one can also use an active infrared source having temperatures of hundreds of degrees Kelvin with the $15\mu$ $CO_2$ band. However, due to the shape of the Planck's Radiation curves, it is highly inefficient and at a diminishing return as the amount of energy available at $15\mu$ from a $800°$ K active source is only $\sim10$ times more than from a $300°$ K passive one.

For pretty much the same reasoning, there is very little chance that a passive infrared source would work well with the effluent gas of Carbon Monoxide (CO) since a $300°$ K source also has very little energy emitted at $4.65\mu$. However, such is not the case for the effluent gas of $H_2O$. Since the absorption band in this case is located at $6.27\mu$, there is still plenty of energy emitted by a $300°$ K source at that wavelength as evidenced by the spectral radiant excitance graph depicted in FIG. 1. Notwithstanding, there are additional impediments that one has to overcome, as will be discussed in more detail below, if one wishes to use the sudden increase in ambient concentration level of $H_2O$ as an indicator for the onset of a fire.

Second, from the Stefan-Boltzmann Law, the total radiant excitance (W–cm$^{-2}$) of a blackbody source is proportional to the 4$^{th}$ power of the absolute temperature T (° K). Thus the total radiant excitance of an 800° K source is (800/300)$^4$ or ~50 times greater than that for an 300° K source. Assuming the detector used is the same for the design of an NDIR gas sensor, the S/N will be degraded by the same factor when a passive infrared source (300° K) is used in lieu of an active infrared source (800° K). Thus the performance of the NDIR gas sensor cannot be expected to be the same for both cases. The one designed with the active infrared source will perform much better because the sensor S/N is expected, at least in theory, to be ~50 times better than that designed with the passive infrared source.

Third and the most significant is to get around the limitation of the Law of Detailed Balance (LDB) or sometimes called the Zeroth Law of Thermodynamics. Relevant to the present discussion, the LDB sets a detection limitation between an infrared radiator (source) having a temperature $T_s$ (° K) and an infrared detector having a temperature $T_d$ (° K). If the source and the detector are separated by vacuum, there cannot be any signal generated by the detector if $T_d = T_s$. It is however possible if $T_d < T_s$. If the source and the detector is separated by a medium (e.g. cloud of gas) having a temperature $T_m$ (° K), the detector signal cannot see any changes as a result of the presence of the gas cloud as long as $T_m = T_s$. However, if $T_m > T_s$, then the detector can generate a signal due to detecting radiation emitted from the gas cloud. Or if the $T_m < T_s$ and the gas cloud contains one or more infrared absorption bands (e.g. $CO_2$ has absorption bands at 4.26µ and 15µ), then the detector signal will change proportional to the amount of radiation absorbed by the gas cloud. The LDB is important and must be taken into consideration if one deals with passive infrared sources having temperatures close to its environ.

To further illustrate the significance of the Law of Detailed Balance, we shall now consider the case of a block of wood with its surfaces painted black (ε~1.0) and a block of aluminum with highly polished surfaces (ε~0.03) being suspended in still air with no or very little contact with surrounding objects except air. Since air is a very poor heat conductor in the absence of convection, the principal heat loss or gain for the blocks is through radiation exchange with its surroundings like the walls, floor or ceiling. It is well-known in physics that an object, having an emissivity value approaches unity (blackbody), radiates (loses) heat very efficiently to its surroundings whose temperature is lower. Conversely it also absorbs (gains) heat very efficiently from its surroundings if the latter's temperature is higher. On the other hand, for an object with very low emissivity value, it gains and loses very little heat radiatively to its surroundings if there is a temperature difference. The Law of Detailed Balance (LDB), however, will ensure that as time progresses indefinitely with no physical changes surrounding the blocks except as earlier described, eventually the temperatures of the blocks, irrespective of their large difference in emissivity, will assume the same temperature as its surroundings.

In practice and it is a common experience that a block of highly polished aluminum always feels colder to the touch than a block of wood, especially when the latter is painted black. The reason can be explained by the difference in their emissivity values. During the night when the temperature is colder, both blocks in the course of time will assume about the same temperature as its surroundings as imposed by the LDB. Then as the temperature rises during the day, the block of wood absorbs heat radiatively much more efficiently than the block of polished aluminum and the latter tends to be colder. Although it is very difficult to predict how much colder will the block of polished aluminum be when compared with the block of wood painted black because it depends on thermal circumstances, it is nevertheless possible, when this fact is combined with the use of the 15µ $CO_2$ or the 6.27µ $H_2O$ absorption band, to design a passive NDIR gas sensor specifically deployed as a very low power fire detector.

FIG. 6 shows schematically the design and implementation of such a passive NDIR gas sensor fire detector without the explicit use of an active radiation source in order to reduce its power consumption to an absolute minimum. This design comprises five main parts. They are respectively a passive infrared source 7, a "waveguide" sample chamber 8, a heat exchanger 9, an infrared detector assembly 10 and signal processing electronics 11. The passive infrared source is essentially a very thin "stretched" film of plastic material 16 having a thickness of ~0.001" or one mil. Plastic materials such as polyethylene, polystyrene etc. are good candidates. However, in order to increase the radiative effectiveness (in term of high emissivity) of the source, only black plastic materials are preferred. Alternatively, a very thin film of black paint with emissivity close to unity can also be applied to just one side of the plastic film.

FIG. 7 shows the construction details of the presently invented passive infrared source. A very thin film (~0.001") of black plastic material 12 (e.g. black polyethylene) is stretched and fitted onto a plastic annular base 13 with the use of a tight-fitting plastic ring 14. Due to the very small mass of the plastic film, its temperature follows closely with that of its surroundings or with the temperature of the effluent gases during the onset of a fire as a result of convection and conduction processes.

Returning now to the currently invented passive gas sensor detector as depicted in FIG. 6, the sample chamber 8 is thermally coupled to one end 15 of the infrared detector assembly 10. An infrared detector 18, either of the thermopile or pyroelectric type, is installed in the center of the detector assembly 10 and facing the far end 17 of the sample chamber 8. For the passive $CO_2$ fire detector, i.e. the effluent $CO_2$ gas is used for its design, the infrared detector 18 uses a spectral filter 19 having an CWL=15.1µ and FWHM=1.0µ as its hermetically sealed window. The detector assembly 10 is in essence a highly polished (ε~0.03) aluminum cylinder approximately one inch in diameter and one inch in length with one end 20 opened to accommodate the infrared detector 18. The other end 21 is opened and shaped as a conical mirror for matching the aperture opening end 15 of the sample chamber 8 with that of the detector 18 (see FIG. 6). Sample chamber 8 is an aluminum waveguide or tubing type with both its inside and outside surfaces highly polished. Since the sample chamber 8 and the detector assembly 10 are thermally coupled together, their temperatures are very close to one another at all times. As discussed earlier, due to the fact that the emissivities of the passive infrared source, 7, and the detector assembly/sample chamber, 10 and 8, are so much different, for most of the time, the former will assume a slightly higher temperature than the latter. Thus the infrared detector 18 actually generates a very small signal viewing the passive infrared source 7 with a slightly higher temperature (typically 1–2° C.) under normal circumstances.

As shown in FIG. 6, the sample chamber 8 is also thermally coupled to a heat exchanger 9. The heat exchanger 9 is also made out of aluminum with both internal and external surfaces highly polished. Its temperature therefore follows closely to those of the sample chamber 8 and the detector assembly 10 and is invariably lower than that of the passive infrared source 7. Along the body of the sample chamber 8 are pairs of openings (holes) 22 covered with a filtering membrane 23 such as a small sheet of polyethylene a few thousandths of an inch thick. These holes allow gases in the vicinity of the heat exchanger 9 to diffuse freely into the sample chamber 8 and exit from same. However, the filtering membrane 23 covering these openings 20 allows only $CO_2$ gas to do so freely. Anything else such as water vapor, dust, smoke particles etc. would be prevented from entering. Any ambient $CO_2$ gas, including the effluent one from a fire, must first diffuse through the heat exchanger 9 which has matching hole locations 24 with those of the sample chamber 8 (one side only as shown in FIG. 6) before entering the sample chamber 8. As the name implies, the function of the heat exchanger 9 is to cool and lower the temperature of the ambient $CO_2$ gas prior to its entrance into the sample chamber 8 for detection.

The present design of the passive $CO_2$ NDIR gas sensor, deployed as a low power, low cost, fast responding and false-alarm resistant fire detector follows the basic guidelines demanded by the Law of Detailed Balance. First, the design guarantees that the temperature of the passive infrared source 7 (see FIG. 6) is always above that for the infrared detector 18 located within the detector assembly 10. This is achieved by making the passive source almost a blackbody ($\epsilon$~1.0) and the detector assembly which houses the detector a very poor heat radiator and absorber ($\epsilon$~0.03). Second, in order for the sensor to detect $CO_2$, assuming that the temperature of the gas will equilibrate rather quickly with that of the sample chamber, the gas must also be cooler than the source. This is achieved by first making the sample chamber 8 a very poor radiator and then thermally decoupled it from the passive source 7. Since the sample chamber 8 and the detector assembly 10 share the same goal of making their temperature lower than that of the passive source 7, they can be thermally coupled together as shown in FIG. 6. Third, in order for the detector to sense a difference in the radiation level from the source when the effluent $CO_2$ from a fire is inside the sample chamber, namely, detect the removal by $CO_2$ of a significant amount of the 15µ radiation emanated from the source, the temperature of the $CO_2$ gas must also be made lower than that of the source according to the LDB. This is achieved with the use of a heat exchanger 9 which is thermally coupled to the sample chamber 8 and hence assumes a lower temperature than that for the source. By making the $CO_2$ gas first pass through the heat exchanger, thereby lowering its temperature to below that for the passive source prior to entering the sample chamber, its presence can therefore be discerned by the detector as an output signal decrease because of the removal of some of the 15µ radiation it normally receives from the source.

The current situation is much enhanced during the onset of a fire. It is because the hot effluent gases which reach the passive infrared source 7 quickly raise its temperature to that of themselves via convention and conduction processes in view of the small thermal mass for the source 7. However, the effluent gases that reach the heat exchanger 9 (see FIG. 6) will hardly change the latter's temperature in the beginning due to its much larger thermal mass. Thus the effluent $CO_2$ gas that finds itself into the sample chamber through the heat exchanger as depicted in FIG. 6 will be much cooler than the passive infrared source 7. In this manner the Law of Detailed Balance restriction of being able to detect the effluent $CO_2$ gas inside the sample chamber due to the onset of a fire by the detector 18 is greatly alleviated.

Although lowering the power consumption of the presently invented passive NDIR gas sensor fire detector is of primary importance, its unit production cost is equally important if it is to successfully replace in the future the environmentally harmful and false-alarm prone radioactive ionization smoke detector. The current design as depicted in FIG. 6 can afford achieving such a goal. First of all, the cost for the passive infrared source 7 is minimal, maybe just a couple cents. The sample chamber 8 and heat exchanger 9 can be extruded as one piece in aluminum with a tool having both the inside and outside surfaces polished. Thus once the tooling cost is defrayed, the unit cost is just the material cost for aluminum (~3 oz. at $1.25/lb). Meanwhile the detector assembly block 10 (see FIG. 5) is expendable without compromising the current design if one chooses to use a special type of thermopile or pyroelectric detector that is directly surface-mountable to the printed circuit board 11. The only pricey item is the infrared detector with the appropriate filter. However, in a massive volume production environment anticipated, both the detector/filter and its associated signal processing electronics should be quite minimal as well. Thus the production cost for the currently invented passive NDIR gas sensor fire detector should be comparable to that for radioactive ionization smoke detectors.

So far the present invention has been discussed in terms of a passive NDIR gas sensor fire detector using one of the effluent gases, namely $CO_2$, generated by a fire. The same inventive concepts can also be applied to another effluent gas of fire, namely water vapor ($H_2O$), if some additional provisions are incorporated into the methodology. First and foremost is the change of the spectral filter installed in the thermopile or pyroelectric detector 18 (see FIG. 6). Instead of using a CWL=15.1µ and FWHM=1.0µ filter for the detection of $CO_2$, a filter having a CWL=6.27µ and FWHM=1.0µ for the detection of $H_2O$ will be used. The other feature that needs to be added to the design illustrated in FIG. 6 is the additional coating of the inside surfaces for the extruded aluminum combined sample chamber 8 and heat exchanger 9 part with a hydrophobic film such as polybutadiene dimethacrylate which is an ultra violate light curable oligomer. The hydrophobic coating prevents the relatively hot water vapor from the fire entering the heat exchanger and sample chamber from condensing and thereby disappearing. Finally, the filtering membrane 23 (see FIG. 6) used to filter out $H_2O$, smoke etc. from the sample chamber 8 is replaced by an oleophobic membrane which allows water vapor and gases to pass through readily but repels dust, dirt and smoke particles from entering.

As we have pointed out before, the current passive NDIR gas sensor fire detector cannot be made to perform as a normally good gas sensor because of its anemic S/N ratio by virtue of the use of a very low temperature passive infrared source. The main objective, however, is only to render it a very low power fire detector by sensing a sudden and significant rise in the concentration level of one of the effluent gases, such as $CO_2$ or $H_2O$, generated by the onset of a fire. Let us now examine how this fire detector will perform in the event of a real fire for the case of using a thermopile detector. With the exception of a very slow-burning and smoldering fire, the temperature in the immediate vicinity of the fire will invariably rise. The passive infrared source of the present fire detector will be the first to be affected by such a rise in temperature by virtue of its very small mass in contact with the hot effluent gases from the fire. On the other hand, the temperature rise at the sample chamber 8, heat exchanger 9 and the detector assembly 10 (see FIG. 6) will only be very minimal due to their relatively large thermal masses. Thus the crucial temperature difference between the passive source and the detector, sample chamber and heat exchanger is steadily increasing during the onset of a fire. As the fire persists, the $CO_2$ or $H_2O$ will eventually get to the vicinity of the fire detector. Since these effluent gases must first pass through the heat exchanger which is by now quite a bit cooler than the passive source, its presence will be readily detected by the detector due to the absorption of radiation from the source that is spectrally coincident with the absorption bands of $CO_2$ or $H_2O$. The characteristic fire signature will therefore comprise the slow rising of the detector signal due to the increase in temperature of the passive source by virtue of the heat of the fire and then it will drop significantly as the much cooler $CO_2$ or $H_2O$ finds its way into the sample chamber via the heat exchanger. Thus by using the trending pattern of the detector output signal, one is able to set a threshold behavior of the output signal for enunciating the onset of a fire. An example of such a fire signature for the enunciation of a fire using the currently invented passive NDIR gas sensor fire detector with a thermopile detector is shown graphically in FIG. 8.

As shown in FIG. 8, the time period prior to the onset of a fire as depicted by the output curve 25 of the thermopile detector of the passive NDIR gas sensor fire detector pretty much reflects the temperature variation of the space in which the fire detector is located. Other than the fact that the output signal might fluctuate high and low as a function of time, it does not exhibit any monotonic temperature trending behavior. After the onset of a fire in the neighborhood as indicated by point 26 in FIG. 8, the temperature of the passive source starts to rise rather quickly leading to a monotonic rise in the detector output as depicted in curve 27. If the fire persists, eventually the effluent gases will reach the heat exchanger and diffuse into the sample chamber of the fire detector. At which point (indicated by circle 28 in FIG. 8) due to the absorption of some of the radiation emanating from the passive source by the effluent gases, the detector output takes a sudden downward turn. This sudden downward turn of the detector output is the fire signature which can be formulated into a quantitative signal threshold that enunciates the onset of a fire.

Essentially the same situation prevails when a pyroelectric detector is used in lieu of a thermopile detector in the design of the presently invented passive NDIR gas sensor fire detector since the pyroelectric detector is an AC detector which can only sense a change in the level of the source radiation received by it. Thus if a pyroelectric detector is used in the fire detector, the fire signature will take on a different form as depicted graphically in FIG. 9. As shown in FIG. 9, the time period prior to the onset of a fire as depicted by the output curve 29 of the pyroelectric detector reflects the temperature variation of the space in which the fire detector is located. The output signal might show some very small amplitude fluctuations representing the small difference in radiation levels from the passive source as received by the detector over time. After the onset of a fire in the neighborhood as indicated by point 30 in FIG. 9, the temperature of the passive source starts to rise rather quickly leading to larger amplitude fluctuations in the detector output curve 31 indicative of larger changes in the radiation level received. If the fire persists, eventually the effluent gases will reach the heat exchanger and diffuse into the sample chamber of the fire detector. At which point (indicated by circle 32 in FIG. 9) the detector output takes a sudden downward turn due to the absorption of some of the radiation emanating from the passive source by the effluent gases in the sample chamber. This is manifested by the AC detector as an easily discernable differential signal 33 as illustrated in FIG. 9. This relatively large AC signal 33 can be used to signal the onset of a fire.

In the above paragraphs the principles needed for designing an NDIR gas sensor fire detector deployed specifically as a very low power fire detector using the 15μ absorption band of $CO_2$ or the 6.27μ absorption band of $H_2O$ but without the use of an active radiation source have been described. There are ways to improve the performance of such a low power fire detector. One example is to deploy a longer path length sample chamber in order to increase the detector voltage drop as one of the effluent gases finds its way into the sample chamber. One might argue that the currently invented fire detector might not be sensitive enough to detect a slow-burning or smoldering fire. However, it is worth pointing out the fact that until a smoldering fire eventually breaks out into an open fire, there is hardly any destructive danger associated with it. But before it gets to that point, the ensuing effluent gases would have been easily detected and the fire enunciation made. It goes without saying that one of the virtues of deploying the presently invented fire detector is the almost complete elimination of false alarms. Furthermore, no longer has one to endure the use of environmentally harmful radioactive Americium-241 (half life of ~400 years) and its potential disposal hazards in the continued use of ionization smoke detectors. Thus the previously insurmountable barriers which have long prevented NDIR gas sensors from being used as fire detectors because of its high power consumption and high cost have now been removed.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A fire detector, comprising:
   a passive NDIR gas sensor that generates a detector signal based upon an absorption band selected from the group consisting of a 15μ absorption band of $CO_2$ and a 6.27μ absorption band of $H_2O$; and
   a heat exchanger to cool gas entering to a sample chamber for measuring a sample gas in said sample chamber; and
   a signal processor which receives the detector signal and generates an alarm signal when a preselected criterion is met.

2. The fire detector of claim 1, wherein the signal processor relies upon a detection algorithm that is based upon a trending pattern of the detector signal indicative of the onset of a fire.

3. The fire detector of claim 2, wherein the detector signal is converted to a DC signal.

4. The fire detector of claim 2, wherein the trending pattern is comprised of a sudden steady increase in the amplitude of the detector signal caused by rising hot air of a potential fire as the fire first breaks out.

5. The fire detector of claim 4, wherein the trending pattern includes a substantial drop in the detector signal strength when an effluent byproduct gas from the fire and smoke particles subsequently arrive near the sensor as the fire persists.

6. The fire detector of claim 1, wherein the passive NDIR sensor is used as a standalone smoke detector.

7. The fire detector of claim 1, wherein the passive NDIR sensor is combined with a smoke detector.

8. A fire detector, comprising:
a passive NDIR sensor that generates a detector signal based upon an absorption band selected from the group consisting of a 15µ absorption band of $CO_2$ and a 6.27µ absorption band of $H_2O$, comprised of:
a passive infrared source with a high emissivity close to 1;
a sample chamber with a low emissivity close to 0.3 thermally decoupled from the passive infrared source; and
an infrared detector located in a detector assembly thermally coupled to the sample chamber;
a heat exchanger thermally coupled to the sample chamber; and
a signal processor which receives the detector signal and generates an alarm signal when a preselected criterion is met;
wherein gas entering the sample chamber passes through the heat exchanger and is at a lower temperature than the temperature of the passive infrared source at an onset of a fire; and
wherein the infrared detector has a detector temperature that is lower than the temperature of the passive infrared source at the onset of a fire.

9. The fire detector of claim 8, wherein the high emissivity is approximately 1.0 and the low emissivity is approximately 0.03.

10. The fire detector of claim 8, wherein internal surfaces of the sample chamber and the heat exchanger are coated with a hydrophobic membrane.

11. The fire detector of claim 8, wherein the difference in temperature between the temperature of the passive infrared source and the detector temperature increases during the onset of the fire.

12. The fire detector of claim 8, wherein the sample chamber and the heat exchanger are formed integrally from aluminum.

13. The fire detector of claim 8, wherein the passive infrared source is comprised of a very thin film of black plastic material.

14. A fire detector, comprising:
a passive $H_2O$ sensor that generates a detector signal representative of attenuation of radiation observed normally from a passive source to the passive $H_2O$ sensor, comprising:
a passive $H_2O$ detector; and
a filter for a 6.27µ absorption band of $H_2O$;
electronics for receiving the detector signal and generating an alarm signal when a preselected criterion is detected by an algorithm based at least in part upon the
an optical aperture to define a subtended solid angle by the passive source; and
a heat exchanger thermally coupled to a sample chamber thermally decoupled from a passive infrared source for lowering the temperature of a sample gas in said sample chamber from that of the passive infrared source.

15. A method for generating an alarm signal in response to a fire, comprising the steps of:
using a passive NDIR gas sensor to generate a detector signal based upon an absorption band selected from the group consisting of a 15µ absorption band of $CO_2$ and a 6.27µ absorption band of $H_2O$ measured in a sample chamber in which a sample gas inside said sample chamber has been cooled to a temperature lower than that of a passive infrared source by a heat exchanger; and
generating the alarm signal when a preselected criterion indicative of the onset of a fire is met based upon an analysis of the detector signal.

16. The method of claim 15, wherein the analysis of the detector signal is performed by using a detection algorithm that relies upon a trending pattern of the detector signal.

17. The method of claim 16, wherein the trending pattern is comprised of a sudden steady increase in the amplitude of the detector signal caused by rising effluent gas of a potential fire as the fire first breaks out.

18. The method of claim 17, wherein the trending pattern includes a substantial drop in the detector signal strength when the effluent gas subsequently arrives near the sensor as the fire persists.

19. A method for generating an alarm signal in response to an onset of a fire, comprising the steps of:
heating a passive infrared source with a high emissivity during the onset of the fire by a hot gas effluent from the fire;
cooling the hot gas effluent from the fire by a heat exchanger and then passing the cooled hot gas effluent into a sample chamber thermally decoupled from the passive infrared source;
using a passive NDIR sensor to generate a detector signal based upon an absorption band selected from the group consisting of a 15µ absorption band of $CO_2$ and a 6.27µ absorption band of $H_2O$; and
generating the alarm signal when a preselected criterion indicative of the onset of a fire is met based upon an analysis of the detector signal;
wherein gas entering the sample chamber is at a lower temperature than the temperature of the passive infrared source at an onset of a fire; and
wherein an infrared detector of the passive NDIR sensor has a detector temperature that is lower than the temperature of the passive infrared source at the onset of the fire.

20. The method of claim 19, wherein the passive infrared source is comprised of a very thin film of black plastic material.

* * * * *